United States Patent
Park et al.

(10) Patent No.: US 8,590,366 B2
(45) Date of Patent: Nov. 26, 2013

(54) APPARATUS FOR MEASURING CONCENTRATION OF $CO_2$ FOR VEHICLE

(75) Inventors: June Kyu Park, Hwaseong-si (KR); Hyun Kim, Hwaseongi-si (KR); Yong Chul Kim, Hwaseong-si (KR); Hee Sang Park, Hwaseong-si (KR); Jun Mo Ku, Hwaseong-si (KR); Moo Yong Kim, Suwon-si (KR)

(73) Assignees: Hyundai Motor Company, Seoul (KR); Kia Motors Corp., Seoul (KR)

( * ) Notice: Subject to any disclaimer, the term of this patent is extended or adjusted under 35 U.S.C. 154(b) by 73 days.

(21) Appl. No.: 13/323,557

(22) Filed: Dec. 12, 2011

(65) Prior Publication Data

US 2013/0086976 A1    Apr. 11, 2013

(30) Foreign Application Priority Data

Oct. 5, 2011    (KR) ........................ 10-2011-0101151

(51) Int. Cl.
*G01N 7/00*    (2006.01)

(52) U.S. Cl.
USPC ........................................ 73/31.01; 73/31.05

(58) Field of Classification Search
USPC ................ 73/23.2, 23.3, 31.01, 31.02, 31.03, 73/31.05
See application file for complete search history.

(56) References Cited

U.S. PATENT DOCUMENTS

| 2009/0039267 A1* | 2/2009 | Arndt et al. | 250/353 |
| 2009/0143923 A1* | 6/2009 | Breed | 701/1 |
| 2010/0025585 A1* | 2/2010 | Taguchi et al. | 250/339.13 |

\* cited by examiner

*Primary Examiner* — Daniel S Larkin
*Assistant Examiner* — Jamar Ray
(74) *Attorney, Agent, or Firm* — Morgan, Lewis & Bockius LLP

(57) ABSTRACT

An apparatus for measuring a concentration of $CO_2$ for a vehicle may include an indoor panel of a vehicle in which an air inlet is mounted, and a $CO_2$ sensing unit mounted in the indoor panel, including a light emitting unit, a light receiving unit, and a case surrounding the light emitting unit and the light receiving unit so as to reflect and move light on a plane, and vertically introduced with air introduced into the inlet with respect to the plane on which light moves.

9 Claims, 3 Drawing Sheets

APPARATUS FOR MEASURING CONCENTRATION OF $CO_2$ FOR VEHICLE

CROSS-REFERENCE TO RELATED APPLICATIONS

The present application claims priority of Korean Patent Application Number 10-2011-0101151 filed Oct. 5, 2011, the entire contents of which application is incorporated herein for all purposes by this reference.

BACKGROUND OF INVENTION

1. Field of Invention

The present invention relates to an apparatus for measuring a concentration of $CO_2$ for a vehicle provided so as to accurately measure a concentration of $CO_2$ in an air in a vehicle.

2. Description of Related Art

Generally, an air conditioner of a vehicle is configured to selectively introduce internal air and external air. However, a contradictory problem is caused according to a selection of the internal/external air introduction apparatus of a vehicle.

That is, when the air conditioner is used as an outdoor air introduction mode, the air conditioner is disadvantageous in summer/winter fuel efficiency and cooling/heating performance and when the air conditioner is used as an indoor air introduction mode, a concentration of $CO_2$ in a vehicle is increased to increase an unpleasant feeling and damage health.

Therefore, the contradiction needs to be solved by actively controlling the internal/external air introduction apparatus of a vehicle so as to be matched with each mode. To this end, an apparatus for measuring a concentration of $CO_2$ in a vehicle is essentially demanded.

However, in order to measure the $CO_2$, it is necessary to collect the indoor air at an appropriate location and measure the collected indoor air through an infrared sensor. The apparatus for measuring a concentration of $CO_2$ for a vehicle according to the related art has not developed a technology with reference to installation position, structure, or the like.

For example, the apparatus for measuring a concentration of $CO_2$ may be disposed at a position approximating to an outlet of an air conditioner, which may lead to different sensing performance due to a difference in a discharge direction of summer/winter air. In addition, the apparatus for measuring a concentration of $CO_2$ needs to be mounted at a position approximating to a respiratory organic of a passenger. In this case, it is necessary to select a position appropriate to sense air of a front seat/a rear seat.

In addition, it is necessary to configure a sensor capable of collecting air according to a flow of air in a vehicle and have an optimized layout according to an operation of an infrared sensor.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

Various aspects of the present invention provide for an apparatus for measuring a concentration $CO_2$ for a vehicle having an optimized layout when mounting a $CO_2$ concentration sensor at an optimized position in a vehicle to sense the concentration of $CO_2$.

Various aspects of the present invention provide for an apparatus for measuring a concentration of $CO_2$ for a vehicle includes an indoor panel of a vehicle in which an air inlet is mounted, and a $CO_2$ sensing unit mounted in the indoor panel, including a light emitting unit and a light receiving unit, surrounding the light emitting unit and the light receiving unit so as to reflect and move light on a plane, and vertically introduced with air introduced into the inlet with respect to the plane on which light moves.

The $CO_2$ sensing unit may be introduced with air from the inside of the vehicle based on the plane on which light moves and discharges the air to the outside of the vehicle.

The reflective film of the $CO_2$ sensing unit may have a polygonal shape surrounding the light emitting unit and the light emitting unit and input the light emitted from the light emitting unit to the light receiving unit by performing the reflection operation plural times.

The $CO_2$ sensing unit may have the light emitting unit mounted on one side thereof and the light emitting unit mounted on the other side thereof and may have an air introduction hole corresponding to the air inlet mounted on the front thereof.

The inside of the indoor panel of the vehicle may be provided with an interruption unit interrupting the transmission of light to the air inlet to prevent the light emitted from the light emitting unit from being leaked to the inside of the vehicle.

The interruption unit may have a cross section shape in which bent pieces are overlappingly disposed in parallel to transmit air and interrupt light.

The air inlet of the indoor panel of the vehicle may be provided with a cover and the cover may be provided with a hooked clamp hooked by being inserted into the inlet and the interruption unit may be indented with a space part 440 in which the hooked clamp is positioned.

The apparatus for measuring a concentration of $CO_2$ for a vehicle may further include a housing mounted in the indoor panel and having the air inlet connected to one side thereof and having an air outlet connected to the other side thereof, wherein the $CO_2$ sensing unit is mounted in the housing 200.

The housing may be formed so that the air outlets are formed at both sides opposite to the air inlet, respectively.

The indoor panel of the vehicle may be an indoor panel of the B pillar of the vehicle.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

The above and other features of the present invention will now be described in detail with reference to certain embodiments thereof illustrated in the accompanying drawings which are given hereinbelow by way of illustration only, and thus are not limitative of the present invention, and wherein.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
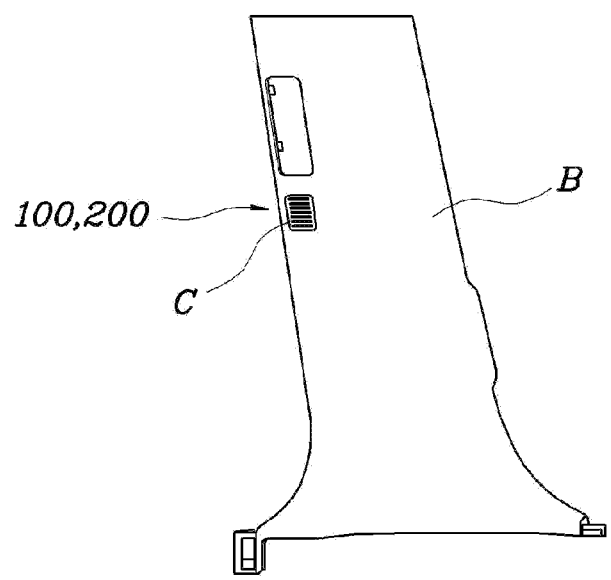
FIG. 1 is a diagram showing a panel in which an exemplary apparatus for measuring a concentration of $CO_2$ for a vehicle according to the present invention is mounted.
Figure 2:
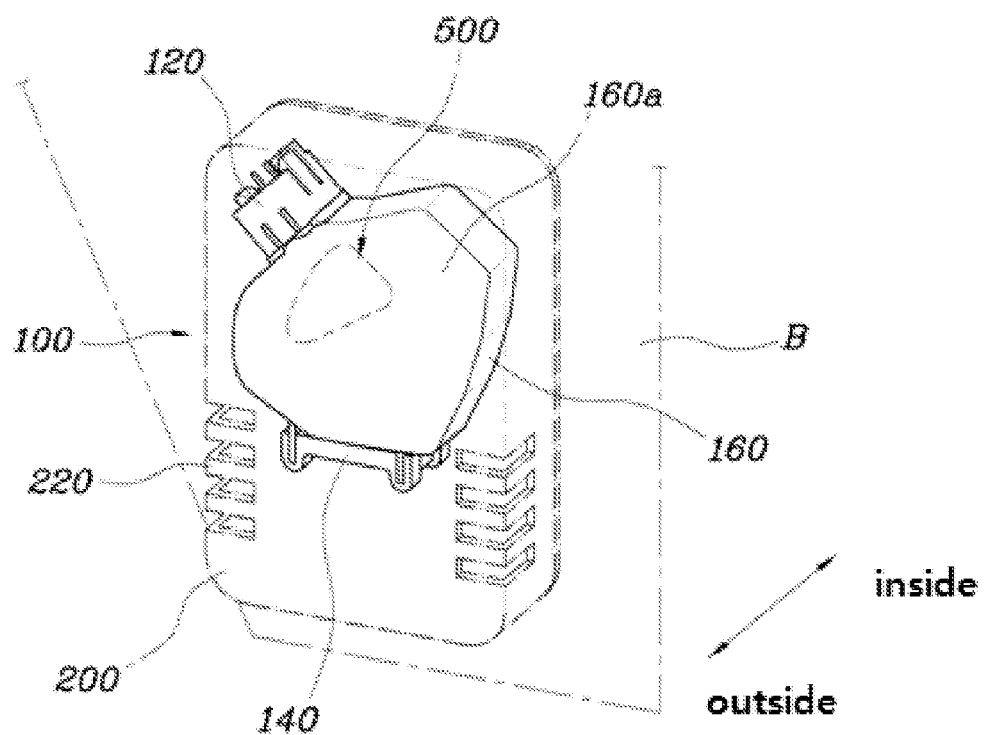
FIG. 2 is a perspective view of the apparatus for measuring a concentration of $CO_2$ for a vehicle shown in FIG. 1 that is viewed from the rear.
Figure 3:
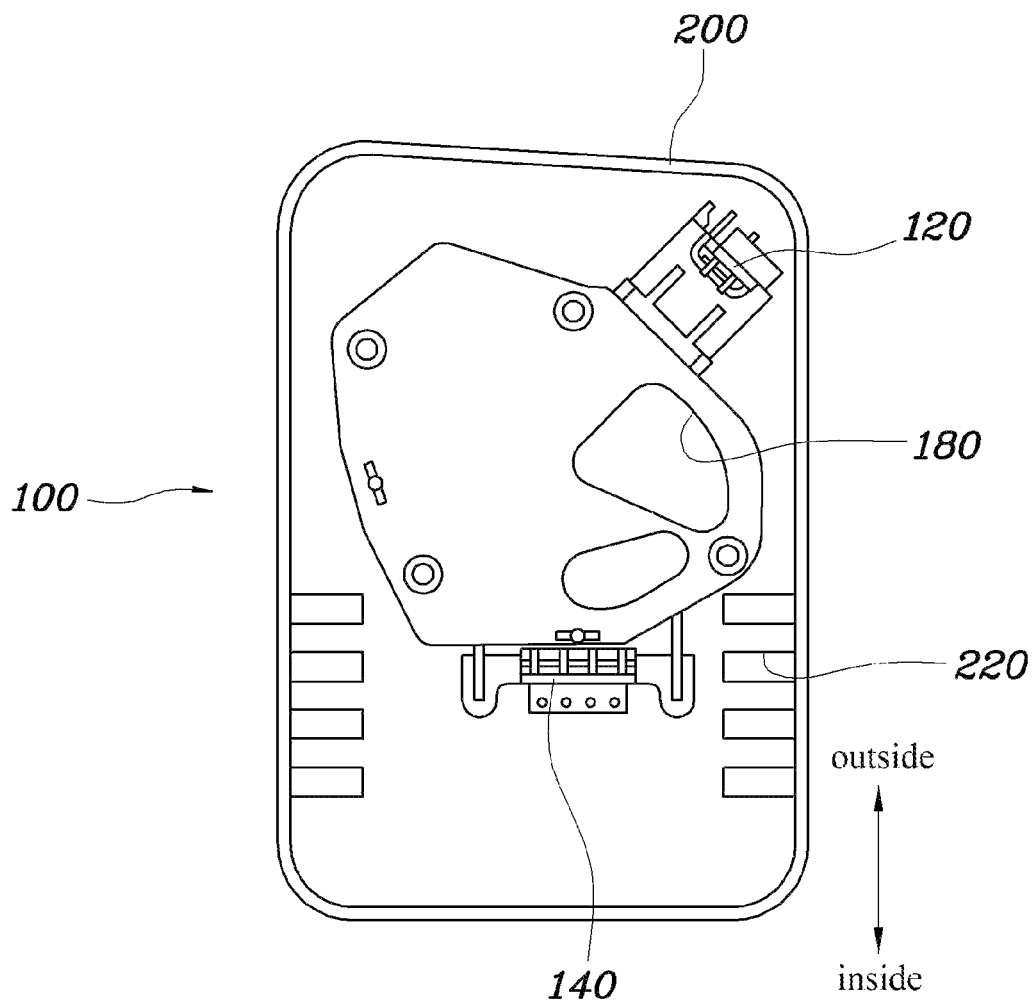
FIG. 3 is a perspective view of the apparatus for measuring a concentration of $CO_2$ for a vehicle shown in FIG. 1 that is viewed from the front.
Figure 4:
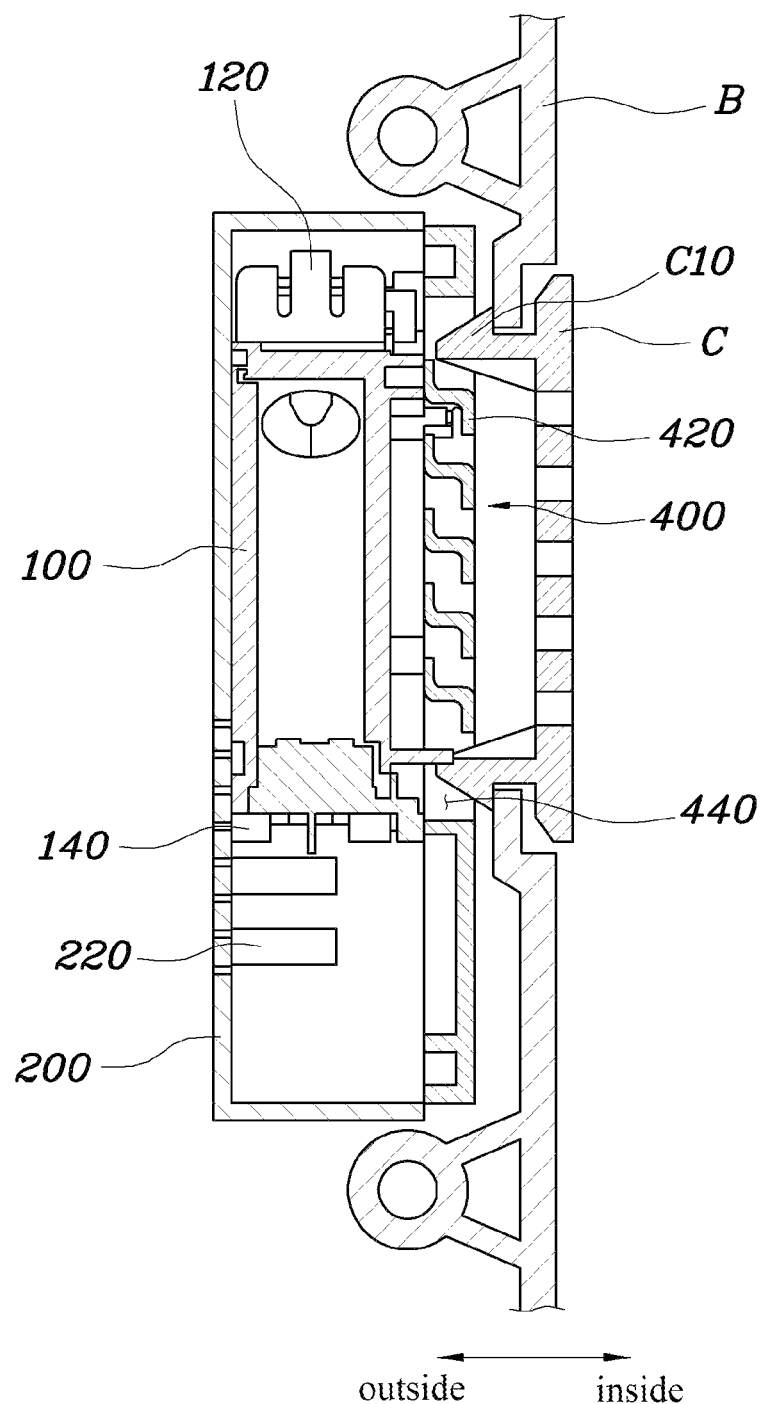
FIG. 4 is a cross-sectional view of the apparatus for measuring a concentration of $CO_2$ for a vehicle shown in FIG. 1.

FIG. 1 is a diagram showing a panel in which the apparatus for measuring a concentration of $CO_2$ for a vehicle according to various embodiments of the present invention is mounted, FIG. 2 is a perspective view of the apparatus for measuring a concentration of $CO_2$ for a vehicle shown in FIG. 1 that is viewed from the rear, FIG. 3 is a perspective view of the apparatus for measuring a concentration of $CO_2$ for a vehicle shown in FIG. 1 that is viewed from the front, and FIG. 4 is a cross-sectional view of the apparatus for measuring a concentration of $CO_2$ for a vehicle shown in FIG. 1.

The apparatus for measuring a concentration of CO2 for a vehicle according to various embodiments of the present invention includes an indoor panel B of a vehicle in which an air inlet 500 is mounted, and a CO2 sensing unit 100 mounted in the indoor panel B of the vehicle, including a light emitting unit 120 and a light receiving unit 140, surrounding the light emitting unit 120 and the light receiving unit 140 so as to reflect and move light on a plane 160a, and vertically introduced with air introduced into the inlet with respect to the plane on which light moves.

In various embodiments, as shown in FIG. 1, the indoor panel B of the vehicle shows a case of an indoor panel of a B pillar of a vehicle. That is, when the apparatus for measuring a concentration of $CO_2$ for a vehicle according to various embodiments of the present invention is mounted in the B pillar of the vehicle, the apparatus for measuring a concentration of $CO_2$ for a vehicle reflects and measures both of inhalation and exhalation of passengers of a front seat and a rear seat, thereby optimizing the effect of measurement.

In addition, the air inlet of the indoor panel B of the vehicle is provided with a cover C and the inside of the cover is provided with a $CO_2$ sensing unit 100.

As can be appreciated from FIGS. 2 to 4, the $CO_2$ sensing unit 100 is provided with the reflective film 160 that is mounted in the indoor panel B, includes the light emitting unit 120 and the light receiving unit 140, surrounds the light emitting unit 120 and the light receiving unit 140 so as to reflect and move light on the plane so as to vertically introduce the air introduced into the inlet with respect to the plane on which light moves.

That is, the air introduced into the cover C of the panel B of the B pillar is vertically introduced to collide with infrared particles and $CO_2$ particles reflected on the plane and wandering therearound, such that the concentration of $CO_2$ may be measured in the light receiving unit 140.

As described above, light is reflected within a closed area without immediately discharging the air by making the light path and the introduced air vertical to each other, thereby obtaining the desired result.

Meanwhile, the $CO_2$ sensing unit 100 is introduced with air from the inside of the vehicle based on the plane on which light moves and discharges the air to the outside of the vehicle. That is, in the case of the discharge, the $CO_2$ sensing unit 100 is performed on the contrary to the above description so that the air is not again introduced into the indoor of the vehicle.

To this end, the reflective film 160 of the $CO_2$ sensing unit 100 is formed to have a polygonal shape surrounding the light emitting unit 120 and the light receiving unit 140 and input the light emitted from the light emitting unit 120 to the light receiving unit 140 by performing the reflection operation plural times and the $CO_2$ sensing unit 100 has a case of which a side forms the reflective film 160. The $CO_2$ sensing unit 100 has the light emitting unit 120 mounted on one side thereof and the light receiving unit 140 mounted on the other side thereof and has an air introduction hole 180 corresponding to the air inlet mounted on the front thereof.

Further, the discharge hole through which air is discharged is separately formed, or otherwise, discharges naturally air between gaps of the parts as shown. However, even in this case, there is a need to prevent the discharged air from being input into the indoor.

In addition, the inside of the indoor panel B of the vehicle is provided with an interruption unit 400 interrupting the transmission of light to the air inlet to prevent the light emitted from the light emitting unit 120 from being leaked to the inside of the vehicle To this end, the interruption unit 400 has a cross section shape in which bent pieces 420 are overlappingly disposed in parallel to transmit air and interrupt light. Further, the cover C is provided with a hooked clamp C10 hooked by being inserted into the inlet and the interruption unit 400 is indented with a space part 440 in which the hooked clamp C10 is positioned.

Therefore, the apparatus for measuring a concentration of $CO_2$ for a vehicle according to various embodiments of the present invention may be mounted even in the inner space of a narrow pillar trim so as no to overlap the layout with the interruption unit 400 that sucks air without discharging light to the outside and is coupled with the cover C to protect the inside thereof.

Meanwhile, the apparatus for measuring a concentration of $CO_2$ for a vehicle according to various embodiments of the present invention further includes a housing 200 mounted in the indoor panel B and having the air inlet connected to one side thereof and having an air outlet 220 connected to the other side thereof, wherein the $CO_2$ sensing unit 100 may be mounted in the housing 200. In addition, the housing 200 may be formed so that the air outlets 220 are formed at both sides opposite to the air inlet, respectively.

Through the above configuration, in the apparatus for measuring a concentration of $CO_2$ for a vehicle according to various embodiments of the present invention, the air is introduced through the cover C and is introduced into the introduction hole 180 and is input to the $CO_2$ sensing unit 100. In addition, the air is discharged through the discharge hole or the gap between the components. Finally, the air is discharged through the discharge hole 220 from the inside of the housing 200 and the flow of air is vertical to the flow of light and the air wanders in the inside of the $CO_2$ sensing unit 100 as maximally as possible while preventing light from being discharged to the outside. In addition, the apparatus for measuring a concentration of $CO_2$ for a vehicle according to various embodiments of the present invention may be firmly mounted even in the inner space of the narrow pillar trim.

For convenience in explanation and accurate definition in the appended claims, the terms front or rear, and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An apparatus for measuring a concentration of $CO_2$ for a vehicle comprising:
   an indoor panel of the vehicle including an air inlet; and
   a $CO_2$ sensing unit mounted on the indoor panel, including a light emitting unit, a light receiving unit, and a case surrounding the light emitting unit and the light receiving unit so as to reflect and direct light on a plane, and vertically introduced with air introduced into the inlet with respect to the plane on which light moves;
   wherein the inside of the indoor panel of the vehicle is provided with an interruption unit interrupting the transmission of light to the air inlet to prevent the light emitted from the light emitting unit from being leaked to the inside of the vehicle.

2. The apparatus of claim 1, wherein air is introduced into the $CO_2$ sensing unit from an interior of the vehicle through the plane, and is discharged to the outside of the vehicle.

3. The apparatus of claim 1, wherein the $CO_2$ sensing unit has a reflective film having a polygonal shape substantially surrounding the light emitting unit and the light receiving unit and directs light emitted from the light emitting unit to the light receiving unit by reflecting the emitted light a plurality of times.

4. The apparatus of claim 1, wherein the $CO_2$ sensing unit has the light emitting unit mounted on one side of the case and the light receiving unit mounted on another side of the case and has an air introduction hole corresponding to the air inlet mounted on a front of the case.

5. The apparatus of claim 1, wherein the interruption unit has a cross section shape in which bent pieces are overlappingly disposed in parallel to transmit air and interrupt light.

6. The apparatus of claim 1, wherein the air inlet of the indoor panel of the vehicle is provided with a cover and the cover is provided with a hooked clamp hooked by being inserted into the inlet and the interruption unit is indented with a space part in which the hooked clamp is positioned.

7. The apparatus of claim 1, wherein the indoor panel of the vehicle is an indoor panel of the B pillar of the vehicle.

8. An apparatus for measuring a concentration of $CO_2$ for a vehicle comprising:
   an indoor panel of the vehicle including an air inlet; and
   a $CO_2$ sensing unit mounted on the indoor panel, including a light emitting unit, a light receiving unit, and a case surrounding the light emitting unit and the light receiving unit so as to reflect and direct light on a plane, and vertically introduced with air introduced into the inlet with respect to the plane;
   a housing mounted in the indoor panel and having the air inlet connected to one side thereof and having an air outlet connected to the other side thereof, wherein the $CO_2$ sensing unit is mounted in the housing.

9. The apparatus of claim 8, wherein the housing is formed so that the air outlets are formed at both sides opposite to the air inlet, respectively.

* * * * *